United States Patent [19]
Mahefky

[11] Patent Number: 5,178,132
[45] Date of Patent: Jan. 12, 1993

[54] LARYNGOSCOPE AND METHOD OF INSERTING A TRACHEAL TUBE

[76] Inventor: Leonard M. Mahefky, P.O. Box 1321, Brackettville, Tex. 78832

[21] Appl. No.: 742,099

[22] Filed: Aug. 2, 1991

Related U.S. Application Data

[63] Continuation of Ser. No. 458,903, Dec. 29, 1989, abandoned.

[51] Int. Cl.$^5$ ............................................. A61B 13/00
[52] U.S. Cl. ....................................... 128/17; 128/15; 128/18
[58] Field of Search ................................. 128/15-20

[56] References Cited

U.S. PATENT DOCUMENTS

| | | | |
|---|---|---|---|
| 718,772 | 1/1903 | King | 128/15 |
| 887,528 | 5/1908 | Schafhirt | 128/15 |
| 1,137,585 | 4/1915 | Craig, Jr. | 128/15 |
| 1,319,904 | 10/1919 | Roberts | 128/15 |
| 1,344,020 | 6/1920 | Bugbee | 128/15 |
| 1,388,170 | 8/1921 | Cameron | 128/16 |
| 1,388,421 | 8/1921 | Forgrave | |
| 2,765,785 | 10/1956 | Pagoto | |
| 3,513,835 | 5/1970 | De Ceuster | |
| 4,052,980 | 10/1977 | Grams et al. | 128/18 |
| 4,064,873 | 12/1977 | Swenson | |
| 4,314,551 | 2/1982 | Kadell | 128/18 |
| 4,425,909 | 1/1984 | Rieser | |

Primary Examiner—Stephen C. Pellegrino
Assistant Examiner—Ralph A. Lewis
Attorney, Agent, or Firm—Charles W. Hanor

[57] ABSTRACT

An improved laryngoscope having a curved laryngeal blade and a chin-engaging member are provided to uniquely employ the chin of a patient as a fulcrum for enabling controlled pivotal movement of the blade. Not only is the laryngeal blade pivotable relative to the chin-engaging member through the operation of plier-like handles, but the blade is also telescopically adjustable to enable use on individuals of varying sizes. A U-shaped blade which is both curved and rounded and a torroidally-shaped chin pad further enhance the operation of the laryngoscope.

11 Claims, 2 Drawing Sheets

LARYNGOSCOPE AND METHOD OF INSERTING A TRACHEAL TUBE

This application is a continuation of co-pending application Ser. No. 07/458,903 filed Dec. 29, 1989, now abandoned.

BACKGROUND OF THE INVENTION

The present invention relates to apparatus and methods for enabling access to the trachea of an individual. More particularly, the present invention relates to apparatus and methods relating to laryngoscopes which enable access to the trachea by displacing the tongue and epiglottis with physical and mechanical control.

Air passage to the trachea of an individual is essential for sustaining life. The trachea is the main passageway through which air passes to and from the lungs of an individual, and its upper portion, the larynx, must be open in order for the individual to breathe in an ordinary fashion. Access to the larynx and trachea is equally important for purposes of respiratory resuscitation. Unfortunately, though, the body of an individual can lose its natural ability or tendency to open the trachea. For instance, when the genioglossus muscle of the tongue relaxes during the administration of general anesthesia, the tongue and epiglottis tend to intract rearward into the throat, thereby obstructing the throat and hindering air passage to the larynx. Similar obstruction may also occur when an individual is suffering a cardiac or respiratory arrest.

Therefore, there is a common need to open and maintain access to the larynx and trachea in a variety of circumstances. Short of a tracheotomy, the only reasonable method known for maintaining such access is through the insertion (or "intubation") of a trachea tube. An intubated trachea tube also greatly facilitates respiratory resuscitation and oscillatory ventilation as well as other medical procedures. A laryngoscope is presently the preferred instrument and provides the preferred method for opening access to the larynx to insert such a trachea tube. With a laryngoscope operatively employed to enable access to the larynx, a trachea tube can be inserted through the mouth and larynx and into the trachea. With the trachea tube in place in the trachea, the laryngoscope can then be removed and the trachea tube maintains the opening of the air passage on its own strength.

Obviously, larngoscopes are helpful whenever access to the trachea is desired, whether for intubation or for other purposes, such as for laryngeal surgery and for administration of medicinal treatments.

A laryngoscope usually consists of a hand grip from which a laryngeal blade extends, supporting a light source. Laryngeal blades come in various shapes, including straight and curved ones, for manually displacing the tongue and epiglottis sufficiently to gain access to the trachea. Consider, for instance, those shown in U.S. Pat. Nos. 4,425,909 and 4,314,551, issued to Rieser and Kadell, respectively. The Rieser patent shows a laryngoscope with a substantially straight blade and the Kadell patent shows a laryngoscope with a curved blade. The square tips of those blades, however, are susceptible to injuring certain internal tissues. Moreover, the specific curvatures of the known laryngeal blades serve predominantly to compress the tongue, while retraction is left to the skill of the individual manipulating the laryngoscope.

Consequently, not only are the shapes of known laryngeal blades critical, but the manner in which they are used is just as critical. The distal end of the blade must reach down into the proximity of the epiglottis and then be pulled forward and/or pressed against the tongue to move the tongue and epiglottis away from the larynx. Once the laryngeal blade of the Rieser laryngoscope is inserted, for example, it is lifted sway from the patient to cause compression of the tongue and epiglottis. The laryngeal blade shown in the Kadell patent, on the other hand, is hinged to a hand grip so that the blade can be manually rotated about its hand grip to displace the tongue. Unfortunately, in the process of performing such movements, an operator of a laryngoscope tends to concentrate on the tip of the laryngeal blade and the remaining portions are often mishandled, causing injuries such as breaking of the patient's teeth, especially the front teeth. Obviously, such an occurrence is undesirable.

To make matters worse, in the course of intubation, once the tongue has been displaced and the epiglottis opened with a laryngoscope, a trachea tube is literally forced into the patient's throat in a hit-or-miss fashion. This can be especially dangerous in emergency situations since a technician, nurse or physician who does not commonly administer anesthesia may only be required to perform intubation once every year or so, and they can easily become unpracticed and sloppy with their technique.

It is, therefore, a primary object of the present invention to improve on present laryngoscopes so that access to and viewing of the trachea (for purposes such as intubation) are enabled for the non-anesthesiologist as well as the generally practicing anesthesiologist who performs intubation almost daily. It is also an object to provide an instrument and a method which make access to the trachea easier, safer and more effective.

Many other objects of the present invention will become obvious to one of ordinary skill in the art in light of this specification, especially when compared with the problems and teachings of the prior art. Other previous laryngoscopes are disclosed in U.S. Pat. Nos. 1,388,421, 4,064,873, and 4,314,551.

SUMMARY

The present invention addresses the foregoing objects and others by uniquely employing the chin of a patient as a reference fulcrum for enabling controlled pivotal movement of a laryngeal blade instead of the normally required upward and forward pulling which is commonly performed in the operation of a laryngoscope. The invention also improves the overall safety and performance of a laryngoscope while ensuring and enabling such pivotal movement by incorporating an adjustable laryngeal blade which may be curved and rounded for insertion into an individual's epiglottic vallecula to engage the root of the tongue and other tissue without injury.

According to the teachings of the present invention, a laryngoscope is provided with a first member, a second member and means for pivoting or otherwise moving the first member relative to the second member in a manner which displaces the tongue and epiglottis of an individual to enable access to or viewing of the individual's larynx or related tissue. The first member includes means for specifically engaging the root of the individual's tongue to retract it from the throat, and the second member comprises means for engaging the individual's chin. The second member may itself be adapted to pivot relative to the chin, either by pivotal engagement or pivotal linkage.

Adjacent a first handle of the apparatus, a mechanical lever may be provided as a second handle so that the laryngeal blade can be easily moved through a desired path relative to the patient's chin. The specific path of such movement is slightly arcuate but depends on the particular features and operation of the first and second members.

All in all, by unique employment of controlled mechanical leverage rather than brute strength, and due to its other aspects including those providing for pivotal movements of the laryngeal blade, an apparatus of the present invention can be operated to simultaneously compress and retract (i.e., draw away from the throat) the tongue in a manner which optimally enables access to the trachea while ensuring the safety of the patient.

There are two embodiments described in the following detailed description. Many other features, alternatives, modifications, substitutions, methods and advantages of the invention will be obvious from that detailed description and the rest of this specification.

DETAILED DESCRIPTIONS OF THE PREFERRED EMBODIMENTS

Figure 1:
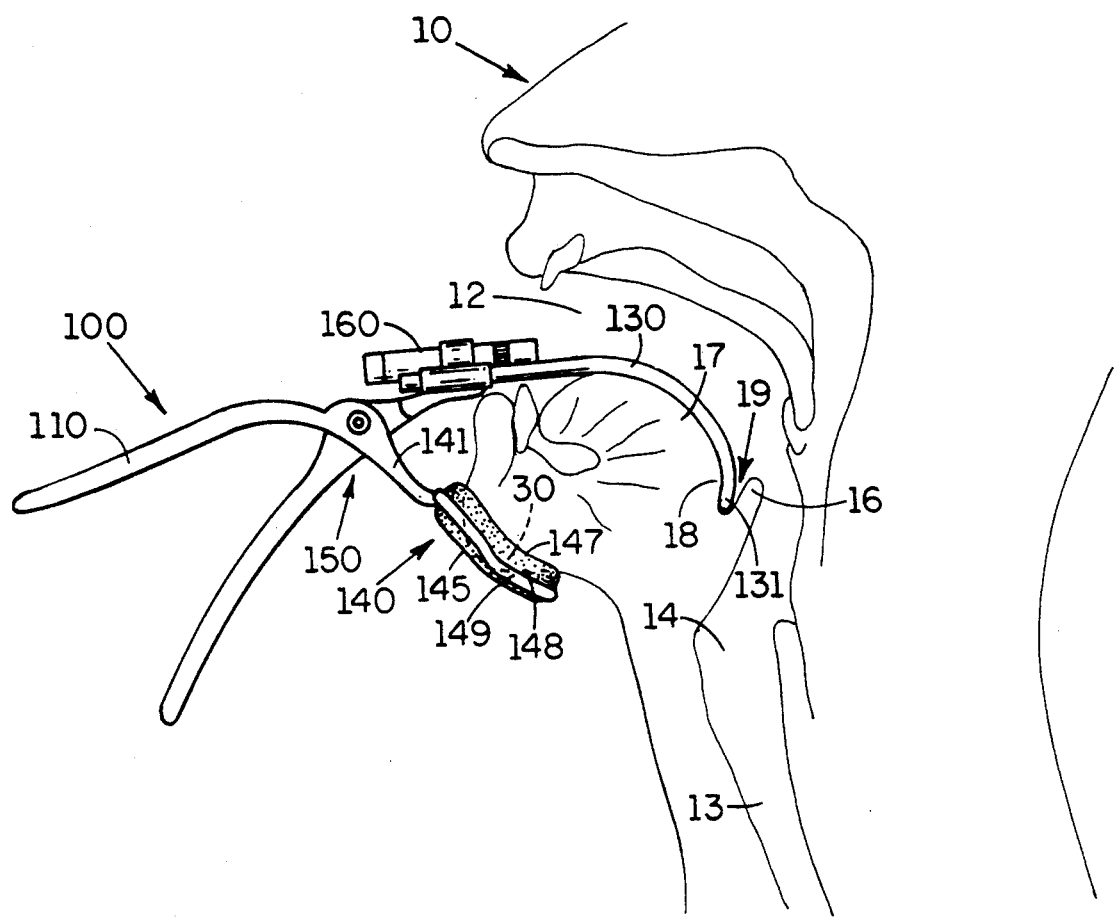
FIG. 1 shows an elevational view of a first embodiment of the present invention as operatively employed relative to an individual 10 to enable access to the trachea 12 of said individual, the individual being shown in sagital section.

Two alternative embodiments 100 and 200 of the invention are shown in FIGS. 1-4. Each of those embodiments 100 and 200 has an upper handle (110 and 210, respectively), a lower handle (120 and 220, respectively), a first member as an adjustable laryngeal blade (130 and 230, respectively), a light source (160 and 260, respectively), and a second member (140 and 240, respectively) comprising a chin-engaging means (145 and 245, respectively). The upper and lower handles of each of the two embodiments 100 and 200 can be manipulated during operation to draw the laryngeal blade 130 and 230, respectively, in an arcuate path generally toward an individual's chin. As is shown and will be further discussed in reference to FIG. 1, such operation causes the respective laryngeal blade to simultaneously compress and retract the tongue of an individual in a manner which causes corresponding retraction of the epiglottis to open access to the individual's larynx and trachea.

For reference purposes, a connection portion 150 and 250, respectively, is designated in each of the two embodiments 100 and 200 and various connections are described relative to the connection portions 150 and 250. Operative movement of each of those embodiments 100 and 200 are, on the other hand, best described relative to the chin of an individual on which the embodiments are used because the chin is employed as a fixed fulcrum in operation. Even though the particular parts in each of the two embodiments 100 and 200 may be similar (in varying degrees) and may be referred to by the same descriptive words, they are numbered differently.

Referring to FIG. 1, the first embodiment 100 comprises a first handle 110, a second handle 120, a first member (or "tongue-engaging member") 130, a second member (or "chin-engaging member") 140, a connection portion 150 and a light source 160. The second handle 120 is integrally formed with the connection portion 150, and the first handle 110 is integrally formed with the second member 140. The first handle 110 is pivotally connected to the connection portion 150 by means of a pivot pin 170 which is rigidly connected to first handle 110 and is pivotally disposed through an aperture 151 in connection portion 150. After pivot pin 170 is in place during assembly, it is secured through connection portion 150 by means standardly known in the art.

Figure 2:
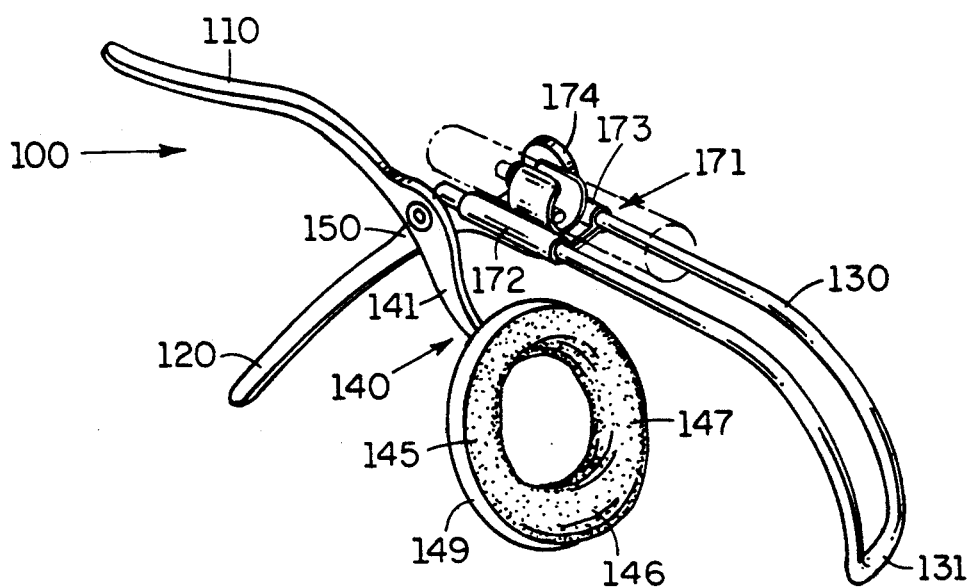
FIG. 2 shows a perspective view of the first embodiment of the present invention.

Referring also to FIG. 2, the chin-engaging means 145 comprises a pad 146 which is composed of a rubber-like material shaped to comfortably engage the chin of an individual on its engaging surface 147. Pad 146, more specifically, has a toroidal shape with a seating surface 148. The seating surface 148 is generally conical but slightly concave and is securely wedged into support 149. Support 149 is substantially circular and is rigidly connected to a shank 141 of second member 140. The shape of pad 146 also enables its pivotal movement in a secure fashion relative to an engaged chin 30 during operation —much like a ball-and-socket joint, with pad 146 acting as a socket receiving the chin 30 as a ball.

Referring to each of the pictured embodiments 100 and 200, the laryngeal blades 130 and 230 are substantially identical in their structure. Similarly the light sources 160 and 260 of each of the embodiments 100 and 200 are substantially identical to one another. Therefore, the structure of those laryngeal blades and light sources of the different embodiments 100 and 200 are described with reference only to the first embodiment 100, as shown in FIG. 2.

Laryngeal blade 130 is basically a slender rod which is bent at its midpoint to form a slender, U-shaped blade (U-shape visible in FIG. 2) shaped much like a hairpin. Such a configuration is advantageous in that its perimeters engage the necessary flesh while its central space enables viewing of the respiratory tract by an operator of the first embodiment 100. The U-shape also enables intubation since the two elongate sides serve as guides for a tracheal tube inserted down its central space. The rounded tip (or bottom) 133 of the U-shape eliminates injury to a patient's internal tissue. Aside from the U-shape, the blade 130 is also bent about a different axis to provide the curved profile visible in FIG. 1. That profile conforms with the normal profile of the upper surface of an individual's tongue and, therefore, enables optimum engagement with the tongue and insertion into the epiglottic valecula during operation. As mentioned, laryngeal blade 130 is substantially identical to laryngeal blade 230.

The two elongated members of laryngeal blade 130 are telescopically inserted through a bracket 171 which is formed integral with connection portion 150. More specifically, bracket 171 includes two parallel sleeves 172 and 173 through which the elongated portions of blade 130 are telescopically inserted to enable slidable adjustment of the position of blade 130 relative to chin-engaging member 140. A locking nut 174 is threadably engaged through a hole in sleeve 173 of bracket 171 for releasably fixing the position of blade 130 relative to bracket 171. As locking nut 174 is tightened into sleeve 173, blade 130 becomes engaged by the shank of locking nut 174, and when locking nut 174 is unscrewed, laryngeal blade 130 becomes relatively free to be slidably adjusted relative to the mounting bracket 171. Such adjustment enables the first embodiment 100 to accommodate individuals who have tissue structures of varying dimensions. Such adjustment also alters the path through which laryngeal blade 130 travels in operation.

Light source 160 is a standardly available type of light source marketed as a "MINI-MAG-LIGHT" and commonly referred to as a "pen light." Specifically, light source 160 is firmly but slidably engaged within a flat spring clamp 161 to bracket 171. Light source 160 is mounted between and parallel to sleeves 172 and 173. In such orientation, light source 160 tends to direct the light beam to ideal locations in the cavities of a patient on which the first embodiment 100 is being employed. Light source 260 of the second embodiment 200 is also a pen light which is also similarly mounted to the laryngeal blade 230 thereof.

Figure 3:
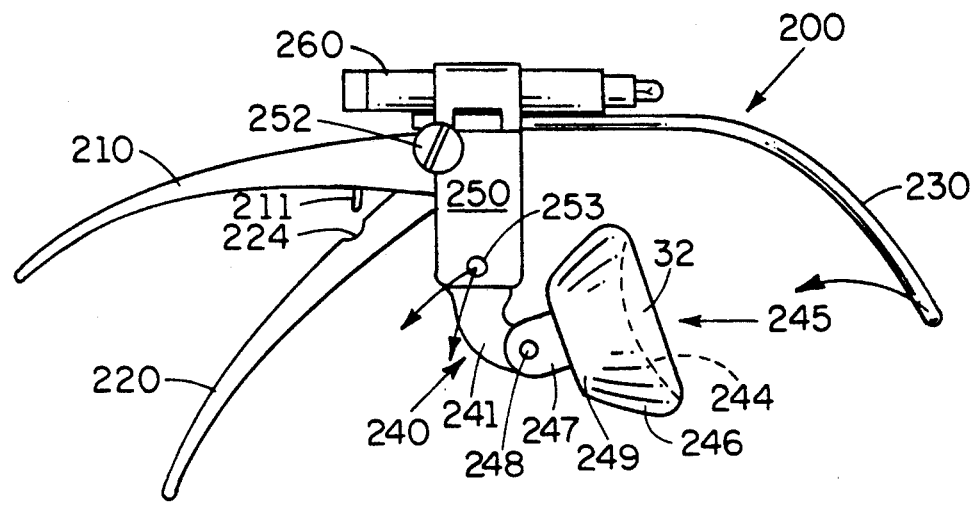
FIG. 3 shows a side elevational view of a second embodiment of the present invention.
Figure 4:
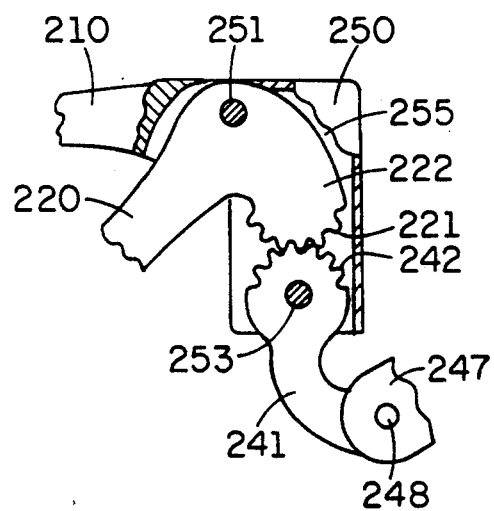
FIG. 4 shows a partially cut-away view of the second embodiment of the present invention, particularly showing the pivotal connections and geared relationship between the second member and the second handle of the second embodiment.

Referring to FIG. 3, the second embodiment 200 comprises a first handle 210, a second handle 220, a first member 230, a second member 240, a connection portion 250 and a light source 260. The first handle 210 is rigidly connected to the connection portion 250. Both second handle 220 and second member 240 are pivotally connected to connection portion 250. Second member 240 is an articulated member which, more particularly, comprises a supporting member 241 and a chin-engaging means 245.

Chin-engaging means 245, itself, comprises a pad 246 having tab 247 protruding therefrom. Pad 246 has a convex outer surface 249 and a concave surface 244 which is for receiving and engaging the chin of an individual. Tab 247 is a metallic member which is embedded in pad 246 on the side of surface 249 for rigid connection therewith. Pad 246 may also be covered by a toroidally shaped cushion for cushioning engagement with a chin. Unlike pad 146 of the first embodiment 100, pad 246 is structured to engage a chin in fixed relation therewith. However, supporting member 241 is pivotally connected to tab 248 by a pivot pin 249.

Both second handle 220 and supporting member 241 are pivotally connected to connection portion 250. Second handle 220 is further engaged with supporting member 241 in a manner such that movement of second handle 220 relative to connection portion 250 causes related movement of supporting member 241 relative to connection portion 250. Referring to FIG. 3, one can see that connection portion 250 encloses a cavity 255 in which second handle 220 and supporting member 241 are pivotally connected. Second handle 220 is pivotally connected to connection portion 250 by means of pivot pin 251. Pivot pin 251 is actually the shank of assembly screw 252 (shown in FIG. 2). Assembly screw 252 is threadably engaged with connection portion 250 and is tightened so that assembly screw 252 is fixed relative to connection portion 250. Supporting member 241 is pivotally connected to connection portion 250 about pivot pin 253, which is rigidly connected to connection portion 250.

Within cavity 255, a portion of second handle 220 is engaged in geared relationship with a portion of supporting member 241. Each of second handle 220 and supporting member 241 are provided with teeth for such engagement. The teeth 242 of supporting member 241 are oriented in an arc about pivot pin 253 and are interdigitated with teeth 221 of second handle 220. The teeth 221 of second handle 220 are oriented in an arc about pivot pin 251 and are of the same pitch as the teeth 242. Thus, when the second handle 220 is pivoted toward first handle 210, supporting member 241 is pivoted toward the laryngeal blade 230. Teeth 221 are actually integral with second handle 220 at the distal end of an arm 222. Arm 222 protrudes away from pivot pin 251 in a direction perpendicular to the longitudinal dimension of second handle 220. Additionally, pivot pin 251 is located as far away from pivot pin 253 as is structurally feasible within cavity 255, and the radius of curvature of the arc in which teeth 242 are oriented is minimized so that small movements of second handle 220 relative to first handle 210 correspond to more substantial movements of supporting member 241. Such geared relationship minimizes the necessary movement of an operator of the second embodiment 200 and, thereby, minimizes the possibilities of injury to a patient on which the second embodiment 200 is employed.

A stop 211 is also provided in the form of a rigid protrusion from first handle 210 toward second handle 220. Second handle 220 is adapted with a notch 224 for receiving the distal end of stop 211 when second handle 220 is pivoted to within a predetermined angular separation therebetween. Alternatively, stop 211 could be pivotally connected to first handle 210 for enabling movement from a first operative position (as shown in FIG. 2) to a second, non-operative position in which stop 211 is not received within notch 224. Thus, when stop 211 would be in its non-operative position, handle 220 could be drawn closely adjacent first handle 210 for compact storage.

To employ the present invention for opening access to the trachea 13 of an individual 10, referring to the first embodiment as shown in FIG. 1, the laryngeal blade 130 is inserted through the mouth 12 of the individual 10 and the chin-engaging means 145 is then positioned to engage the chin 30 of the individual 10. Once chin-engaging means 145 engages the chin 30, the chances that the laryngoscope 100 will injure individual 10 are significantly minimized. Then, the position of the laryngoscope 100 as a whole (or, more particularly, the position of connection portion 150) is pivotally adjusted relative to the chin 30 in a manner such that the tip of laryngeal blade 130 is positioned in the region of the epiglottis 16 of the individual. The light source 160 can be quite helpful in this stage of the employment of laryngoscope 100. Ideally, the tip 131 of laryngeal blade 130 is inserted into the epiglottic vallecula 19 to engage tongue 17 at its root 18. Once the tip 131 of laryngeal blade 130 appears to be overlapping the epiglottis 16, the first handle 110 and the second handle 120 are manipulated to draw the laryngeal blade 130 into compressive engagement with the root 18 of the tongue 17 so that the tongue 17 as a whole is compressed and the root 18 thereof is drawn generally toward the chin 30 in a manner which, in turn, retracts the epiglottis 16 to open access to the trachea 13. Thus, blade 130 is easily manipulated through a slightly arcuate path in which it simultaneously compresses the tongue 17 and retracts the tongue 17 and epiglottis 16.

In the process of this latter step (i.e., the manipulation of first handle 110 and second handle 120 to draw the laryngeal blade 130 generally toward the chin-engaging means 145), the operator of the laryngoscope 100 focuses attention on the laryngeal blade 130 and simultaneously adjusts the position of connection portion 150 in a manner such that the laryngeal blade 130 travels through a slightly arcuate path in the general direction of the chin 30. The resulting movement is a pivoting (counterclockwise in FIG. 1) of the laryngoscope 100 about the chin 30. Such an adjustment in the position of connection portion 150 is not only natural, but the squeezing of the handles 110 and 120 toward one another in operation tends to cause such movement. The same is true of the second embodiment 200. Thus, with each of the embodiments 100 and 200, not only does the respective laryngeal blade 130 and 230 pivot and/or translate relative to the connection portion 150 and 250, but that connection portion, itself, pivots relative to the chin of a patient during operation. By balancing those two degrees of pivotal movement, an operator of a laryngoscope of the present invention can easily optimize the compression and retraction of the tongue and epiglottis for enabling access to the trachea. Nevertheless, through any of such movements, the likelihood of injury to the patient is minimized since the embodiments 100 and 200 are anchored to the relatively fixed fulcrum of the patient's chin 30.

In the first and second embodiments 100 and 200, the connection portions 150 and 250, in turn, act as planetary fulcrums about which the respective laryngeal blade 130 and 230 pivots. For instance, referring to the second embodiment 200, as the first handle 210 and second handle 220 are drawn together, the supporting member 241 rotates about pivot pin 249 which is a substantially stationary fulcrum relative to a patient's chin during operation. The laryngeal blade 230, in turn, rotates relative to supporting member 241 about the connection of pivot pin 253. The result is that, during operation, laryngeal blade 230 moves in an arcuate path generally toward the patient's chin, as indicated by arrows B. For another example, as the first handle 110 and the second handle 120 of the first embodiment 100 are drawn together, the pivot pin 170 in operation is pivoted about a patient's chin, and the laryngeal blade 130 would translate in a corresponding arcuate path generally toward that chin. As the laryngeal blade 130 moves through the resulting slightly arcuate path, it optimally displaces the tongue and epiglottis in a manner which tends to draw the epiglottis away from the larynx 14 of the individual 10.

Many other alternatives, alterations, substitutions, variations, modifications, equivalents and combinations of the preferred embodiments and their various elements will be obvious to one of ordinary skill in the art in light of this specification, including the drawings and the claims, and in light of the prior art. For instance, various features of each of the preferred embodiments could be employed with features of the other preferred embodiments to accomplish the invention and to enable other obvious advantages according to the teachings of the present invention. For a specific example, connections equivalent to the pivotal connection of the pad 246 to the supporting member 241 in the second embodiment 200 could be employed in the first embodiment 100 so that the chin-engaging means 145 could further accommodate the chin of an individual during operation of the first embodiment 100. Similarly, other aspects which are known in the art could be combined or substituted for features of the preferred embodiments without departing from the essence of the invention. All of the foregoing and more fall within the scope of this invention and the invention should, therefore, not be limited by the foregoing descriptions, but rather should be defined by the following claims.

What is claimed is:

1. A laryngoscope comprising a tongue engaging member adjustably connected to a pivoting means for extending to a desired length for engaging the root of a tongue of an individual;
   a chin engaging member connected to said pivoting means for engaging the chin of said individual;
   said pivoting means operable to pivot said tongue engaging member relative to said chin engaging member causing displacement of the epiglottis of said individual by said engaging member to provide access to the trachea of said individual;
   said tongue engaging member comprises a laryngeal blade;
   said laryngeal blade is curved to enable insertion within the epiglottic vallecula of said individual;
   wherein said member for engaging the chin of said individual is adapted to pivot relative to said chin.

2. The laryngoscope of claim 1 wherein said laryngeal blade is slidably connected to said pivoting means for enabling adjustment of the position of said blade relative to said chin-engaging member.

3. A laryngoscope comprising a tongue engaging member adjustably connected to a pivoting means for extending to a desired length for engaging the root of a tongue of an individual;
   a chin engaging member connected to said pivoting means for engaging the chin of said individual;
   said pivoting means operable to pivot said tongue engaging member relative to said chin engaging member causing displacement of the epiglottis of said individual by said tongue engaging member to provide access to the trachea of said individual;
   said tongue engaging member comprises a laryngeal blade;
   said laryngeal blade is curved to enable insertion within the epiglottic vallecula of said individual;
   wherein said member for engaging the chin of said individual is adapted to pivot relative to said chin;
   wherein said pivoting means comprises the first handle connected to said blade wherein said blade is slidable relative to said first handle and the second connected to said chin engaging member, said first and second handles being pivotally connected wherein movement of said second handle toward said first handle causes movement of said blade towards said chin engaging member.

4. A laryngoscope comprising a tongue engaging member adjustably connected to a pivoting means for extending to a desired length for engaging the root of a tongue of an individual;
   a chin engaging member connected to said pivoting means for engaging the chin of said individual;
   said pivoting means operable to pivot said tongue engaging member relative to said chin engaging member causing displacement of the epiglottis of said individual by said tongue engaging member to provide access to the trachea of said individual;
   said tongue engaging member comprises a laryngeal blade;
   said laryngeal blade is curved to enable insertion within the epiglottic vallecula of said individual;

wherein said member for engaging the chin of said individual is adapted to pivot relative to said chin; wherein said pivoting means comprises a connection portion, wherein said blade is adjustably connected to said connected portion and section engaging means is pivotally connected to said connection portion; a first handle rigidly connected to said connection portion and a second handle pivotally connected to said connection portion.

5. The laryngoscope of claim 4 wherein said chin-engaging member is connected to said second handle wherein movement of said second handle toward said first handle causes movement of said chin-engaging member relative to said connection portion and toward said tongue-engaging member.

6. The laryngoscope of claim 5 further comprising means for supporting said chin-engaging member, said supporting means being pivotally connected to said connection portion and having teeth integral therewith which are interdigitated with teeth of said second handle for moving said supporting member in relation with movement of said second handle.

7. The laryngoscope of claim 6 further comprising means for limiting the movement of said blade relative to said second handle for moving said supporting member.

8. The laryngoscope of claim 7 wherein said limiting means comprises a stop positioned between said first handle and said second handle for limiting the movement of said second handle relative to said first handle.

9. A laryngoscope comprising a tongue engaging member adjustably connected to a pivoting means for extending to a desired length for engaging the root of a tongue of an individual;
a chin engaging member connected to said pivoting means for engaging the chin of said individual;
said pivoting means operable to pivot said tongue engaging member relative to said chin engaging member causing displacement of the epiglottis of said individual by said tongue engaging member to provide access the trachea of said individual;
said tongue engaging member comprises a laryngeal blade;
said laryngeal blade is curved to enable insertion within the epiglottic vallecula of said individual;
wherein said member for engaging the chin of said individual is adapted to pivot relative to said chin;
further comprising a light source mounted to said first member for directing light onto the internal tissue of said individual; wherein said pivoting means is adapted to pivot said laryngeal blade relative to said second member in the manner which simultaneously compresses and retracts the tongue of said individual wherein said laryngeal blade is telescopically connected to said pivot means for enabling adjustment of the position of said blade relative to said chin engaging member.

10. The laryngoscope of claim 9 further comprising a set screw for selectively preventing movement of said blade relative to said pivoting means.

11. A laryngoscope comprising a tongue engaging member adjustably connected to a pivoting means for extending to a desired length for engaging the root of a tongue of an individual;
a chin engaging member connected to said pivoting means for engaging the chin of said individual;
said pivoting means operable to pivot said tongue engaging member relative to said chin engaging member causing displacement of the epiglottis of said individual by said tongue engaging member to provide access to the trachea of said individual;
said tongue engaging member comprises a laryngeal blade;
said laryngeal blade is curved to enable insertion within the epiglottic vallecula of said individual;
wherein said member for engaging the chin of said individual is adapted to pivot relative to said chin;
further comprising a light source mounted to said first member for directing light onto the internal tissue of said individual: wherein said pivoting means is adapted to pivot said laryngeal blade relative to said second member in the manner which simultaneously compresses and retracts the tongue of said individual wherein said laryngeal blade is telescopically connected to said pivot means for enabling adjustment of the position of said blade relative to said chin engaging member; said blade comprises a U-shaped member having a round tip; said U-shaped member is curved to match the surface of an individual's tongue for insertion of said tip in the epiglottic vallecula near the root of said tongue; wherein said laryngeal blade is telescopically connected to said pivoting means for enabling adjustment of the position of said blade relative to said chin engaging member further comprising a said screw for selectively preventing telescopic movement of said blade relative to said pivoting means.

* * * * *